United States Patent [19]

Gortz et al.

[11] 4,332,264
[45] Jun. 1, 1982

[54] AUTOMATED CLEANING SYSTEM FOR DIALYZERS

[75] Inventors: Norman Gortz, Irvine; Andrew S. Huson, Tustin; Robert M. MacIntyre, Anaheim, all of Calif.

[73] Assignee: United Healthcare Association, Newport Beach, Calif.

[21] Appl. No.: 126,522

[22] Filed: Mar. 3, 1980

[51] Int. Cl.³ .......................... B08B 3/04; B08B 9/00
[52] U.S. Cl. ............................ 134/57 R; 134/113; 134/171; 210/140; 210/321.5
[58] Field of Search .............. 134/2, 22 R, 22 C, 56 R, 134/57 R, 58 R, 113, 166 R, 166 C, 171; 210/140, 321.5

[56] References Cited

U.S. PATENT DOCUMENTS

| | | | |
|---|---|---|---|
| 2,827,724 | 3/1958 | Edds | 134/57 R X |
| 2,878,969 | 3/1959 | Griswold | 406/133 |
| 3,352,779 | 11/1967 | Austin | 210/646 |
| 3,441,136 | 4/1969 | Serfass | 210/90 |
| 3,462,361 | 8/1969 | Greenwalt | 128/214 A |
| 3,563,381 | 2/1971 | Edelson | 128/214 R |
| 3,700,491 | 10/1972 | Higley | 428/394 |
| 3,753,493 | 8/1973 | Mellor | 210/321.5 |
| 3,827,926 | 8/1974 | Stana | 156/242 |
| 3,871,913 | 3/1975 | Shaldon | 134/22 R |
| 3,946,731 | 3/1976 | Lichtenstein | 128/214 R |
| 3,992,301 | 11/1976 | Shippey | 210/23 H |
| 4,018,684 | 4/1977 | Uffer | 210/140 |
| 4,113,614 | 9/1978 | Rollo | 210/22 A |
| 4,153,554 | 5/1979 | von der Heide | 210/96 M |
| 4,158,034 | 6/1979 | Riede et al. | 134/22 C X |
| 4,166,031 | 8/1979 | Hardy | 134/22 C X |
| 4,209,402 | 6/1980 | Gentles | 210/140 X |
| 4,227,886 | 10/1980 | Bullock et al. | 134/22 R X |

FOREIGN PATENT DOCUMENTS 2294716 7/1976 France ........................... 134/2

Primary Examiner—Robert L. Bleutge
Attorney, Agent, or Firm—Knobbe, Martens et al.

[57] ABSTRACT

A fully automated system for cleaning and disinfecting blood dialyzers is disclosed.

12 Claims, 5 Drawing Figures

AUTOMATED CLEANING SYSTEM FOR DIALYZERS

BACKGROUND OF THE INVENTION

The invention generally relates to a method and apparatus for cleaning artificial dialyzers which are employed as artificial kidneys in dialysis treatments.

At present, the three general types of dialyzers which are known and available are the hollow fiber, parallel plate, and coil type dialyzers.

The hollow fiber dialyzer consists of multiple mutually parallel tubular membranes in close proximity to one another. The core of the fibers comprise the blood side of the dialyzer and the channels formed by their exteriors from the dialysate side. Parallel plate dialyzers consist of a series of parallel planar membranes. The membranes divide the dialyzer into alternating blood and dialysate sides. The coil type dialyzer consists of at least two membranes rolled into a spiral configuration. This configuration produces concentric circular pathways which form alternating blood and dialysate compartments.

After a dialysis treatment has been completed various membranes of the dialyzer are filled with a mixture of saline and blood. Historically, dialyzers in general were not thought to be reusable after the dialysis treatment. However, there have been attempts to design manual and/or semi automatic systems which would wash and disinfect/sterilize the dialyzer in preparation for a subsequent dialysis treatment.

One such attempt is disclosed in U.S. Pat. No. 3,753,493 issued to Mellor. This patent discloses a dialyzer apparatus which has a clean water inlet and an inlet for introducing cleaning and/or sterilizing liquids. Such liquids are then delivered into the water stream and circulated in parallel through the dialysate and blood sides of the dialyzer in one direction. A timer is used to control the sequential delivery of the water flow and cleaning liquid through the dialyzer. This controller is simply a clock which sequences the steps of the cleaning process.

U.S. Pat. No. 3,871,913 issued to Shaldon discloses another system for cleaning a dialyzer. In Shaldon, a dialysis fluid, fresh water and sterilizing fluid are respectively introduced into the dialyzer for respectively washing, rinsing and sterilizing it.

Both the Mellor and Shaldon systems fail to provide the necessary identification, monitoring, control and versatility necessary to produce a truly safe, efficient and practical dialyzer cleaning system. For example, neither system provides tests during the cleaning process to determine whether the dialyzer meets certain reusability criteria.

The systems lack the capacity to automatically machine sequence a repetition of cleaning steps or to automatically augment the cleaning steps depending upon whether the dialyzer passes or fails these reusability criteria. The systems do not provide for differing cleaning processes for the different types of dialyzers, nor do they provide for the simultaneous application of differing cleaning steps to the blood and dialysate sides of a particular dialyzer. In addition, the systems also lack the capacity to automatically inhibit the cleaning sequences if the dialyzers are in a non-reusable condition. Finally, although it is known that a dialyzer should be reused only with the same patient, the systems lack safety checks necessary to insure that the proper patient will receive the proper dialyzer, and that, if any failures in the system occur, they will be fully traceable and will not be used to inhibit any further cleaning.

As a consequence of the ineffectiveness of prior systems, dialyzers are routinely discarded after each dialysis treatment, thus, making the cost of such treatments even more expensive.

There is, therefore, a distinct need for a fully automated dialyzer cleaning process and apparatus which will provide safe, efficient, versatile and controlled cleaning of dialyzers.

SUMMARY OF THE INVENTION

The disclosed invention obviates the above deficiencies in previous devices by providing a fully automated cleaning system usable with all of the three currently available dialyzer types: parallel plate, coil and hollow fiber.

The inventive process comprises two phases: an identification phase and a cleaning phase. In the identification phase, an identification of the patient who has a particular dialyzer is made to insure that said particular dialyzer will be reused only with that same patient. This patient number is also stored and used to determine the number of times the particular dialyzer has been cleaned; i.e., reused. Additionally, the dialyzer type is identified to allow the cleaning sequence to be tailored for the particular type of dialyzer. The system can provide multiple, simultaneously operating cleaning stations and, therefore, as part of the identification phase, the particular station number used to clean each dialyzer is identified and stored to provide traceability.

The cleaning phase comprises a predetermined sequence of steps, typically broken into sub-sequences, which are selectable for cleaning the particular types of dialyzers. An important feature of the invention is that the cleaning sequences used to clean parallel plate and coil type dialyzers differ from that used to clean hollow fiber dialyzers. This is due to the recognition that the planar membrane interfaces of the parallel plate and coil dialyzers permit and require differing cleaning steps from the tubular configuration of the hollow fiber type.

The cleaning sequence comprises plural rinsing and disinfecting/sterilizing steps, interspersed with blood presence, pressure leakage tests and volume or ultrafiltration rate analyses. Failure of the dialyzer to meet any of the predetermined criteria necessary to pass these analyses results in the repetition of cleaning sub-sequences, or the rejection of the dialyzer as non-reusable and an inhibition of the cleaning sequence. The system is also capable of simultaneously applying different cleaning procedures to the blood and dialysate sides of the dialyzer being cleaned.

The apparatus employed for practicing the invention is a fully automated, modular machine to which additional stations may be added to provide simultaneous cleaning of multiple dialyzers. The flow of air, cleaning, disinfecting and/or sterilizing fluids is regulated by a series of valves and pumps which are, in turn, controlled by the electronics of the system. Each station is capable of operating independently, the electronics providing monitoring, recording and logging functions for all stations.

The system, therefore, has the capability of providing different cleaning processes for differing types of dialyzers, for performing various reusability checks to determine whether the cleaning process is proceeding properly, and has the ability to inhibit the further sequencing or to add additional cleaning sequences if the various tests are not passed. If any malfunction in the system occurs during the operation, the operator is made aware of the site of the problem by means of various malfunction indicators. The system, therefore, insures that a dialyzer is properly cleaned, is ready for reuse, and is returned for use only with the proper patient.

These and other advantages will become more apparent in the discussion below, which makes reference to the following set of drawings, wherein.

DETAILED DESCRIPTION OF THE PREFERRED EMBODIMENTS

Figures 1, 1A:
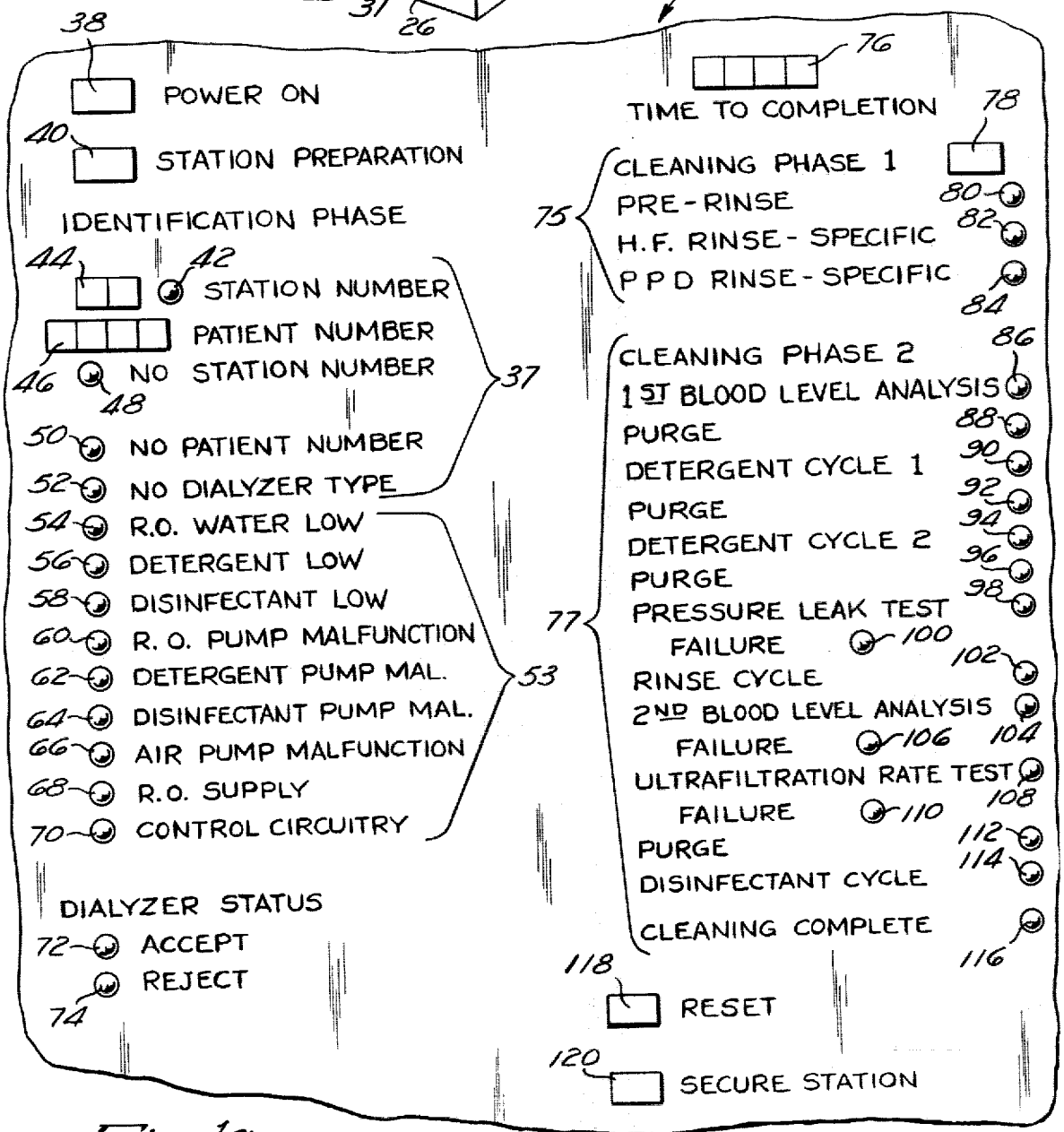
FIG. 1 is a perspective view of the dialysis cleaning machine, including the front control panel.
FIG. 1a is an enlarged, elevation view of the front control panel shown in FIG. 1.

Referring to FIG. 1, the dialyzer cleaning apparatus is shown generally as 10. The apparatus 10 has two cleaning stations 12 and 14, and may include any number of additional cleaning stations. Thus, the apparatus 10 is modular in concept, so that a selectable number of dialyzers may be washed simultaneously.

Each station 12, 14 is capable of washing any type of dialyzer. As shown in FIG. 1, parallel plate dialyzers 16, 18 are shown connected to stations 12, 14 respectively for cleaning. A coil type dialyzer or hollow fiber type dialyzer (not shown) could equally well be attached to either station 12, 14. Each of these dialyzer types includes a dialysate side and blood side, each provided with a connector for attachment to an arterial and a venus tube. An arterial blood side tube 24, and a venus blood side tube 26 extend from the fluid flow control devices within the apparatus 10 for connection to the dialyzers 16, 18. A photo-optical input is produced by a digital data reading wand 30 which reads digital data from a label 31 which identifies the dialyzer type, patient number and dialyzer serial number or equivalent identification.

The cleaning apparatus 10 also includes a front panel 36 which contains a number of gauges, switches, lights and displays, as more clearly shown in FIG. 1a. A power-on switch 38 may be pressed by an operator to activate the apparatus 10. Thereafter, the operator may activate a station preparation switch 40 to prepare the particular station 12, 14 for the cleaning of a dialyzer 16, 18 prior to the dialyzer 16, 18 connection. The panel 36 also includes a number of switches and lights 37 for control and monitoring of the identification phase of the process. These include a station number switch 42 which is pressed to actuate a display 44, which provides the station number. It should be understood that there will be a different station number switch for each particular station. The switch 42 also records this station number within the system electronics, as described below. A patient number display 46 is provided to notify the operator of the patient number read by the wand 30. Three lights 48, 50, 52 are provided to warn the operator that (a) no station number has been identified, (b) no patient number has been identified, and (c) no dialyzer type has been identified respectively.

The next group of lights 53 indicates that there is a malfunction in the system. Thus, lights 54–70 are individually labled on the panel 36 to notify the operator of the nature of any malfunction. The specific purpose of each light in the group 53 will be described below.

The next two lights 72, 74 indicate the status of the dialyzer being cleaned. Accept light 72 indicates that the status of the dialyzer is acceptable and reject light 74 indicates that the dialyzer has been rejected for a particular failure as will be described.

In the second column of the panel 36, a time to completion display 76 indicates the total time needed to complete an entire cleaning cycle.

The next two series of lights and switches 75, 77 provide the operator with a visual indication of the cleaning plate in progress during two distinct cleaning phases which are described below. Lights 80–98, 102, 104, 108, 112 and 114 thus show the cycle in progress, while lights 100, 106 and 110 alert the operator of analysis failures. A switch 78 is used to begin the cleaning process.

Finally, a cleaning complete light 116 indicates that the entire cleaning phase is complete.

The remainder of the panel 36 consists of a reset switch 118 which is manually actuated by the operator to reset the cleaning apparatus 10 to the beginning of the cleaning phase, ready for another cleaning operation. Finally, secure station switch 120 is manually actuated by the operator when the system is to be shut down.

Figure 2:
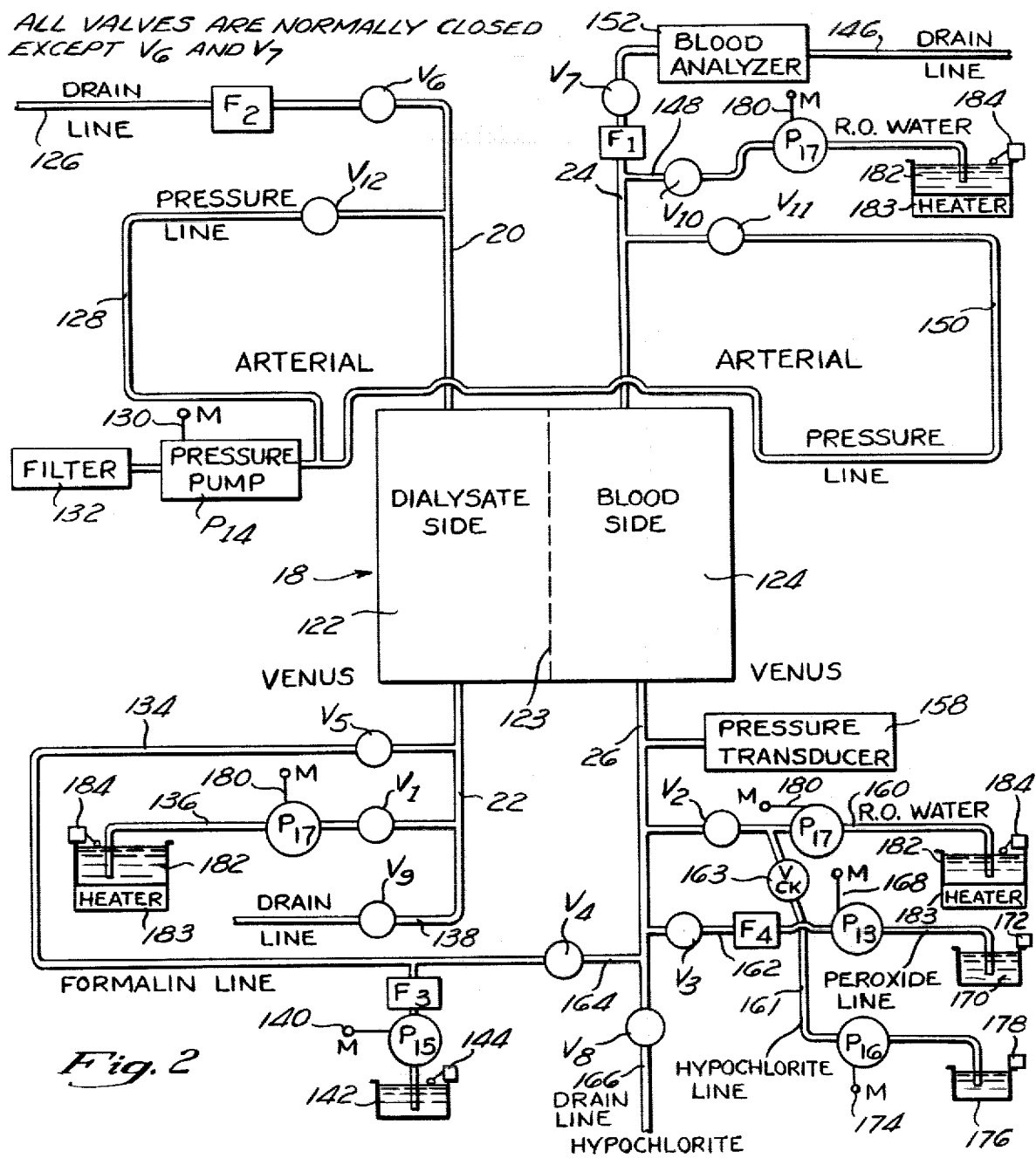
FIG. 2 is a schematic diagram of the mechanical elements of the machine shown in FIG. 1.

Referring now to FIG. 2, the hydraulic and pneumatic control elements of the apparatus 10 may be described. A dialyzer 18 is shown schematically in the center of the figure, and involves a dialysate side 122 and a blood side 124 separated by a membrane 123. This dialyzer may be any type, i.e., parallel plate, coil or hollow fiber.

The arterial dialysate side tube 20 is connected to a drain line 126, leading to a drain or sewer system, and a pressure line 128 leading to a pressure pump $P_{14}$ which has a malfunction sensor 130. The flow of fluids through the drain line 126 is controlled by a valve $V_6$, while the rate of flow of fluid through the drain line 126 is measured by a flow meter $F_2$. The rate of flow of air through the pressure line 128 is regulated by valve $V_{12}$. The air which flows through pressure line 128 may be supplied from a reservoir (not shown), and is filtered by means of a filter 132.

The venus dialysate side tube 22 is connected to a formalin supply line 134, an R.O. water (i.e. reverse osmosis water) supply line 136, and a drain line 138. Formalin is pumped through the formalin line 134 from a reservoir 142 by means of a formalin pump $P_{15}$. The flow of formalin being measured by a flow meter $F_3$. A sensor 140 monitors any malfunction in the formalin pump $P_{15}$, while a formalin supply sensor 144 provides a warning when the quantity of formalin is low.

The arterial blood side tube 24 is connected to a drain line 146, an R.O. water line 1148 and an air pressure line 150. Flow of a fluid through the drain line 146 is controlled by valve $V_7$. The drain line 146 also includes a blood analyzer unit 152 and a flow meter $F_1$. A pump $P_{17}$ supplies R.O. water to the line 148 from a reservoir 182, the flow being controlled by a valve $V_{10}$. A valve $V_{11}$ connects the pressure pump $P_{14}$ to the tube 24.

The venus blood side tube 26 is connected to a pressure transducer 158 which is used for the pressure leak and ultrafiltration rate tests described below. The tube 26 is connected to an R.O. water supply line 160 and a hypochlorite line 161 through a valve $V_2$, a peroxide line 162 controlled by a valve $V_3$ and monitored by a flow valve $V_4$, a formalin line 164 and a drain line 166. A hydrogen peroxide pump $P_{13}$, monitored by a malfunction sensor 168, is used to pump hydrogen peroxide through the peroxide line 162 from a reservoir 170, which includes a level indicator 172. A sodium hypochlorite pump $P_{16}$, monitored by a malfunction sensor 174, is used to pump a detergent such as sodium hypochlorite through a one way check valve 163 in the hypochlorite line 161 from a reservoir 176, monitored by a level sensor 178.

The flow of formalin from the pump $P_{15}$ through the formalin line 164 is regulated by a valve $V_4$, and is measured by a flow meter $F_3$. The rate of flow fluid through the drain line 166 is controlled by valve $V_8$.

R.O. water is pumped through each of the R.O. water lines 136, 148 and 160 by means of an R.O. water pump $P_{17}$, including a malfunction sensor 180, connected to a R.O. water reservoir 182 which has an R.O. water supply indicator 184. If desired, the R.O. water contained in R.O. water reservoir 182 may be heated to approximately 60° F.-70° F. by a heater 183. As is well known to those in the art, an R.O. water producing machine (not shown) supplies R.O. water to reservoir 182. It should also be understood that an acceptable alternative to the R.O. water is soft water.

Relating FIG. 2 to FIG. 1a, when the R.O. water supply is low, as indicated by R.O. water supply indicator 184, R.O. water low light 54 is lit. When either the supply of peroxide or sodium hypochlorite is low, as indicated by peroxide supply indicator 172 and sodium hypochlorite supply indicator 178, respectively, detergent low light 56 is lit. Disinfectant low light 58 indicates that the supply of disinfectant is low as indicated by formalin supply indicator 144. When R.O. pump malfunction sensor 180 indicates that the R.O. pump $P_{17}$ is malfunctioning, R.O. pump malfunction light 60 is lit. When either peroxide pump malfunction sensor 168 or sodium hypochlorite pump malfunction sensor 174 indicates that the perioxide pump $P_{13}$ or sodium hypochlorite pump $P_{16}$ are malfunctioning, detergent pump malfunction light 62 is lit. Disinfectant pump malfunction light 64 indicates that the formalin pump malfunction sensor 140 senses that the formalin pump $P_{15}$ is malfunctioning. When air pressure pump malfunction sensor 130 indicates a malfunction in the pressure pump $P_{14}$, air pump malfunction light 66 is lit. If any malfunction develops in the R.O. water producing machine, the R.O. supply light 68 is lit.

It should be understood that, although formalin is the preferred sterilizing medium, any of the well known disinfectants for sterilizing, such as glutaraldehyde are acceptable. It should also be understood that other detergents other than sodium hypochlorite are acceptable. The preferred detergent is a sodium hypochlorite sold and manufactured under the trademark Clorox Bleach by Purex Corporation. Similarly, although hydrogen peroxide is the preferred oxidizing medium, any oxidizing medium which is non-pyrogenic, nonexplosive, nontoxic and is compatible with a dialyzer membrane is acceptable, such as, glutathione.

Figure 2A:
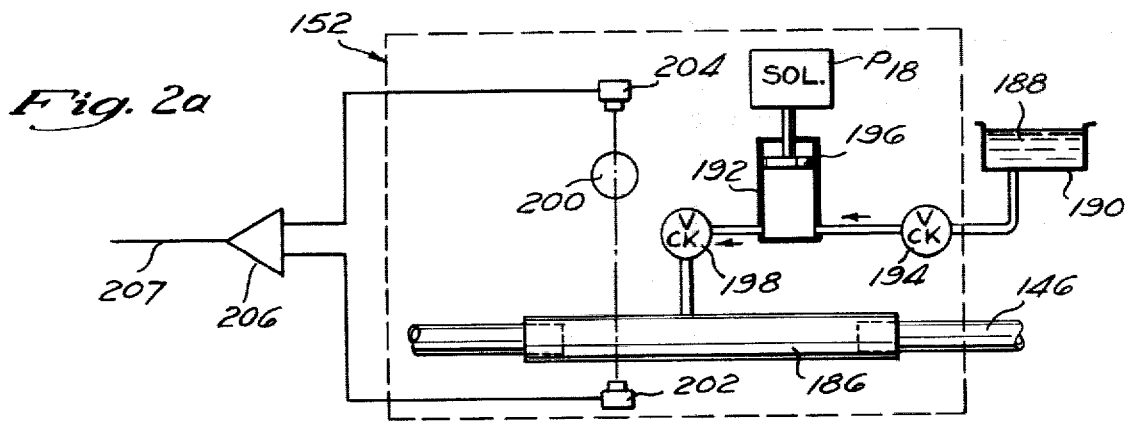
FIG. 2a is a more detailed schematic diagram of the blood analyzer shown in FIG. 2.

Referring now to FIG. 2a, the details of the blood analyzer 152 will be described. The blood analyzer 152 includes a clear plastic tubular insert 186 which forms a length of the arterial blood side drain line 146. A chemical reagent 188 is contained in a reservoir 190, and flows into a cylinder 192 through a check valve 194. A piston 196 in the cylinder 192 is reciprocated by a solenoid $P_{18}$. When piston 196 is raised in the cylinder 192, chemical reagent 188 is drawn into the cylinder 192. Then, as the piston 196 is forced downward by the solenoid $P_{18}$, the chemical reagent 188 within the cylinder 192 is forced into the plastic insert 186 through another check valve 198, which when forced into the plastic insert 186, mixes with the wash effluent and turns color with the presence of blood. The cylinder 192 permits an accurately measured quantity of reagent to be admitted to the insert 186 during each cycle of the solenoid $P_{18}$.

A light source 200 is positioned to illuminate the plastic insert 186 and its contents. A first photocell 202 is positioned to measure the light passing through the insert 186 from the source 200. A second photocell 204 is positioned to directly measure the level of the light 200. The first photocell 202 and second photocell 204 are connected as inputs to a differential amplifier 206. The differential amplifier measures a difference in electrical output from the first photocell 202 and second photocell 204 to compare the amount of light which reaches the two photosensors. This, in turn, is dependent upon the amount of blood in the fluid within the insert 186 which will produce the color change in the chemical reagent 188. When the differential amplifier senses a given voltage difference, a signal is produced on output line 207. It will be understood that the use of the two photocells 202, 204 and amplifier 206 cancels out the effects of changing brightness of the source 200.

The entire cleaning procedures will now be described in reference to several tables, and FIGS. 1a, 2 and 2a. In the first step in the process, the operator manually actuates the power on switch 38. Next, the operator manually actuates the station preparation switch 40.

The next sequence of steps, steps 3-11, comprise the station preparation cycle sequence, which is set forth in Table I, and which occurs without a dialyzer 18 connected to the apparatus.

Thus, during this cycle, the arterial dialysate side line 20 is connected to the venus dialysate side line 22 and the arterial blood side line 24 is connected to the venus blood side line 26 by means of jumper tubes shown on FIG. 2. Table I describes the control sequences, functions and step time for steps 3 through 11. The first, far left-hand column of Table I indicates the step number. The second column indicates the time, expressed in seconds, for each particular step. The third column indicates the control sequence which is performed on the blood side of the dialyzer 124, while the fourth column reflects the resulting blood side function. The fifth column indicates the control sequence for the dialysate side 122 of the dialyzer, and the final, sixth column indicates the resulting dialysate side function.

Figure 3:
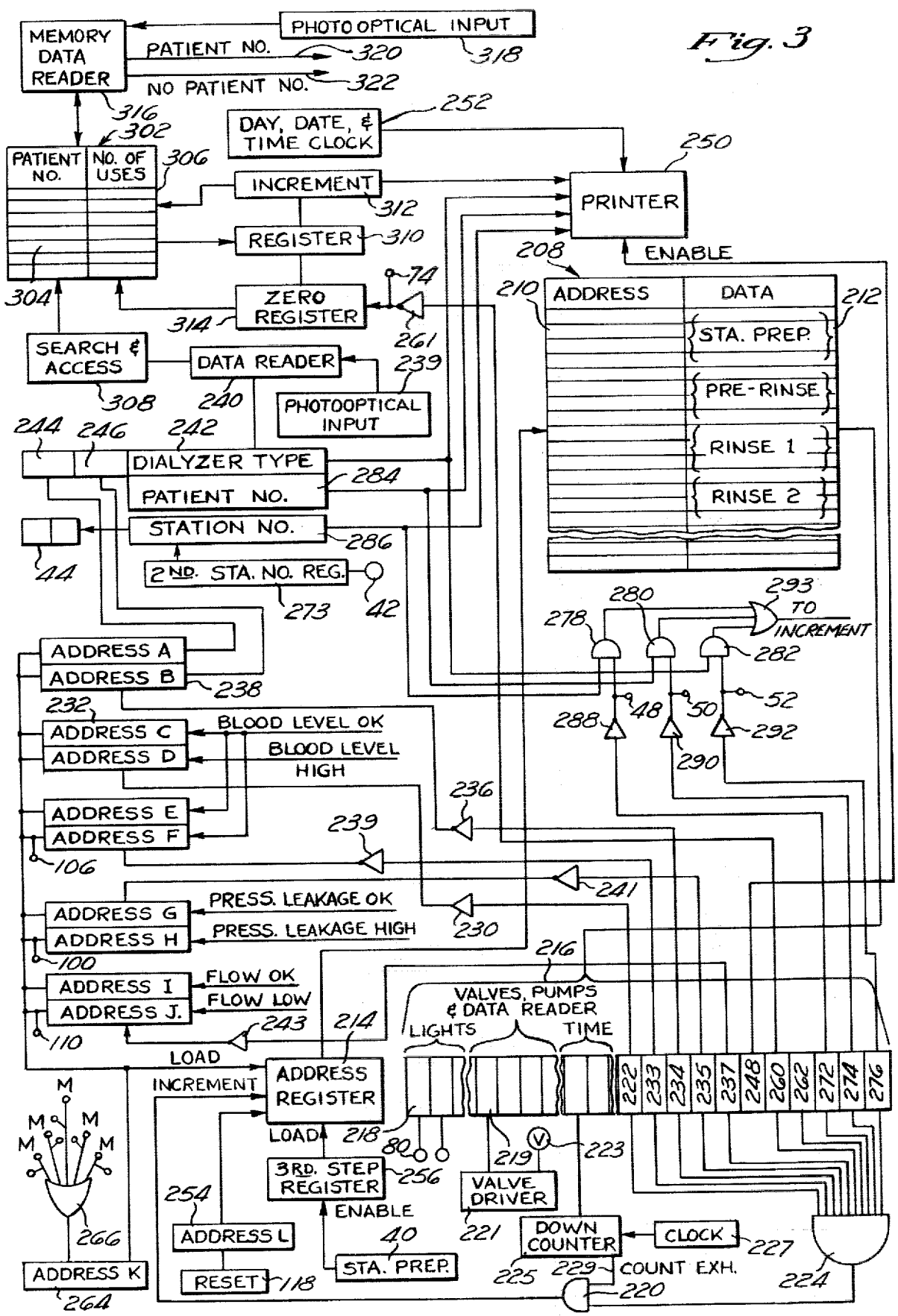
FIG. 3 is a schematic diagram of the electronics of the machine shown in FIG. 1.

As will be understood from the detailed description of FIG. 3 below, the steps of Table I, as well as the remaining tables, now to be described, are automatically controlled by an electronic sequencing system, except where manual actuation is described. Thus, once initiated, the cleaning cycles proceed, in sequence, automatically.

Referring to Table I, Step No. 3, which requires seventeen seconds, is performed by turning on the R.O. water pump $P_{17}$ and opening valves $V_2$ and $V_1$. The normal position of the valves $V_1$ through $V_{12}$ is normally closed, except for $V_6$ and $V_7$, which are normally open. The normal state of the pumps $P_{13}$ through $P_{17}$ is off. Opening the valve $V_2$ allows R.O. water to flow through the blood side 24 of the dialyzer 18, producing a forward rinse as a blood side function. Similarly, opening the valve $V_1$ allows R.O. water to flow through R.O. water line 136 to the dialysate side 122 of dialyzer 18, producing a forward rinse on the dialysate side.

Step 4 requires thirty-four seconds. On the blood side 124, the control sequence is to close valve $V_7$, open valve $V_8$ and open valve $V_{11}$. The air pressure pump $P_{14}$ is turned on. These control sequences produce an air purge through the pressure line 150, which continues through the blood side 124 of the dialyzer. On the dialysate side 122, the valve $V_1$ is opened and the pump $P_{17}$ is actuated to continue the forward rinse.

Step 5 requires thirty-four seconds. The blood side control sequence closes the valve $V_7$, opens the valve $V_8$, closes the valve $V_{11}$ and opens the valve $V_{10}$. In addition, the R.O. water pump $P_{17}$ is actuated. This produces a reverse rinse of R.O. water through the blood side 124 of the dialyzer 18. With respect to the dialysate side 122, the valve $V_1$ remains open and the pump $P_{17}$ remains on to produce a forward rinse.

Step 6 requires the thirty-four seconds to complete. The functions on both the blood side 124 and dialysate side 122 are forward rinses and are obtained in the same manner as in Step 3.

Step 7 requires thirty-four seconds. The blood side function is an air purge and the dialysate function is a forward rinse which are obtained in the same manner as in Step 4.

Step 8 requires thirty-four seconds. The blood side function is a reverse rinse and the dialysate side function is a forward rinse which are obtained in the same manner as in Step 5.

Step 9 requires thirty-four seconds to complete. The functions on both the blood side 124 and dialysate side 122 are forward rinses, and are obtained in the same manner as in Step 3.

Step 10 requires thirty-four seconds. The blood side 124 function is an air purge and the dialysate side 122 function is a forward rinse, obtained in the same manner as Step 4.

Step 11 requires thirty-four seconds to complete. It produces a reverse rinse on the blood side 124 and a forward rinse on the dialysate side 122, and is produced by the same sequencing as found in Step 5.

This completes the preparation cycle for the system.

The next step, Step 12, requires the operator to manually disconnect the jumpers and connect the dialyzers 18 to their stations.

At the next step, Step 13, the operator manually presses the station number button 42, which will then indicate the station number on the display 44. If the station number is not depressed, the light 48 will light, and further sequencing is inhibited. The recording of the station number allows the system electronics, described below, to determine at which station the particular dialyzer 18 was cleaned. This provides system traceability, so that, if any problem occurs, for example, in a dialysis treatment with a particular dialyzer which has been cleaned, the faulty station may be determined and repaired.

Step 14 requires the manual inputing of the patient number, which is displayed in the patient number display 46. The patient number is composed of the last four digits of a person's social security number, and is attached, in the form of a machine readable code, on label 31, to the particular dialyzer. The patient number is read by providing a photo-optical input from a device such as a reading wand 30, well known in the art. If no patient number is entered, the "no patient's number" light 50 will light, and the system electronics will inhibit any further sequencing. The patient's number also provides a means of determining the number of times a particular dialyzer has been cleaned. Thus, the patient's number is stored, and the system electronics counts the number of times each patient number is stored. The patient number is also extremely important in that, when the particular dialyzer after cleaning, is to be used again in a dialysis treatment, a reading wand is used to sense the patient's number. If, for any reason, that dialyzer has been rejected by the apparatus 10 during cleaning, the patient number is automatically dropped from the memory. Thus, a comparator, as will be described later, functions to compare the incoming patient number with the stored patient numbers. If no corresponding patient number is found, the "no patient number" light 50 will light, indicating to the operator that that particular dialyzer should not be used.

Step 15 involves entering the dialyzer type. This is done by means of the reading wand 30 or other suitable photo-optical input which reads an alphabetical designation that is placed on the dialyzer itself in machine readable form. Thus, for example, H.F. would indicate a hollow fiber dialyzer; P.P.D. would indicate a parallel plate dialyzer and C.O. would indicate a coil dialyzer. This dialyzer type is in the system electronics, and is used to determine the proper cleaning sequence, as will hereinafter be described. If no dialyzer type is entered, "no dialyzer type" light 52 will illuminate, and will inhibit any further sequencing.

Thus, in order for the cleaning process to begin, the electronics must be provided with a complete set of identifications, from Steps 13, 14 and 15.

Once the identification process is complete, cleaning phase 1 is initiated, and the time required to complete the cleaning process will be automatically displayed on the "time to completion" display 76.

Step 16 comprises manually actuating the cleaning phase 1 with switch 78. The first portion of cleaning phase 1 is a prerinse cycle which is composed of Steps 17 through 25. During the prerinse cycle, the prerinse light 80 is lit. These are outlined in Table II. One will note that the Steps 17 through 25 of the prerinse sequence are the same as Steps 3 through 11 of the station preparation cycle.

Thus, the valving and pump sequencing will not be discussed again. It will be understood that the Steps 17 through 25 consist of three, three step cycles. On the blood side 124, the cleaning cycle is to apply a forward rinse, an air purge and then a reverse rinse. All three cleaning steps function to dislodge and flush away blood components from the dialyzer membranes. The air purge serves the additional function of removing moisture from the blood side 124. Traditionally, cleaning procedures have employed fluid flushes in one direction only. However, this inventive process employs rinsing in both directions which has been found to increase the agitation of the dialyzer membranes, thereby producing a cleaner dialyzer in a shorter period of time. The dialysate side function throughout Steps 17-25 is a forward rinse which not only serves to flush the dialysate side, but also provides a counterbalancing pressure against the pressure produced by the blood side functions. This fluid pressure helps to prevent a rupture of membranes which would tend to occur without such counterbalancing pressure.

Upon completion of the prerinse sequence, the system electronics will select a cleaning sequence that is specific to the attached dialyzer type. Thus, there is a rinse cycle which is specific to a hollow fiber type of dialyzer, and another rinse cycle which is specific to parallel plate and coil type dialyzers.

Table III reflects the cleaning sequence specific to a hollow fiber type dialyzer which will now be described. Step 26 requires four minutes to complete. The blood side control sequence opens the valve $V_8$, which opens the venus blood side drain line 166. The dialysate side control sequence opens the valve $V_1$, closes the valve $V_6$, and turns on the R.O. water pump $P_{17}$. With the valve $V_1$ open and the pump $P_{17}$ on, a forward rinse is provided on the dialysate side 122. However, the closing of the valve $V_6$ provides a build-up of pressure within the dialysate side 122. Thus, with the venus blood side drain line 166 open, this fluid pressure being exerted against the membrane wall 123 of the dialyzer, causes a squeezing of the blood side 124.

This squeezing of the blood side 124 has been found to be a highly effective cleaning step by serving to dislodge and to expel blood components from the blood side of the dialyzer. The physical configuration of the hollow fiber membrane permits the utilization of such pressure. This step is not employed with parallel plate and coil dialyzers since as presently manufactured, their flat membrane interfaces would tend to rupture under this squeezing.

Step 27 requires two minutes to complete. The blood side control sequence is to close the valve $V_7$, open the valve $V_8$ and to open the valve $V_{10}$. In addition, the R.O. water pump $P_{17}$ is activated. This produces a reverse rinse in the blood side 124. The dialysate side 122 control sequence opens the valve $V_9$. This produces a drain open condition in which the venus dialysate side drain line 138 is open.

Step 28 requires two minutes to complete. The blood side control sequence opens the valve $V_2$ and turns on the R.O. water pump $P_{17}$, which produces a forward rinse on the blood side 124. On the dialysate side 122, the valve $V_9$ remains open, so that the dialysate side function is a drain open position.

Step 29 requires four minutes to complete and is the same as Step 26, in which the dialysate side 122 function is a forward rinse which squeezes the blood side 124, which has venus blood side drain line 166 open.

Step 30 requires two minutes to complete and is the same as Step 27, having a reverse rinse on the blood side 124, and a drain open condition on the dialysate side 122.

Step 31 requires two minutes to complete and is the same as Step 28, having a forward rinse on the blood side 124 and a drain open condition on the dialysate side 122.

This completes the specific sequencing for a hollow fiber type of dialyzer. During this hollow fiber specific rinse, "hollow fiber rinse" light 82 is lit.

Table IV illustrates Steps 32-35, the rinse sequence specific to parallel plate and coil type dialyzers. Thus, if a parallel plate or coil type dialyzer is being cleaned, the system, after completing Step 25, will automatically sequence to Step 32.

Each of the four steps requires four minutes to complete. The sequence consists of two, two step subsequences. Each sub-sequence applies first a forward and then a reverse rinse to the blood side 124. As has been discussed, the cycling of forward and reverse rinses has been found to be quite effective in the removal of blood components from the dialyzer membranes. The dialysate side function throughout the sub-sequence is a drain open condition in which the drain lines 138 and 126 are open.

This completes the parallel plate and coil type dialyzer specific rinse sequence. During this sequence, the "parallel plate dialyzer rinse" light 84 is on.

With the completion of the specific rinse program, the sequence continues with the common, main cleaning steps of the cleaning process, referred to as cleaning phase 2 on the panel 36.

Table V contains the sequence cleaning phase 2, which is common to all types of dialyzers. It begins with Step 36, which requires one minute to complete. This step is generally the first blood level analysis.

Step 36 follows either Step 31 in the case of a hollow fiber dialyzer or Step 35 in the case of a parallel plate or coil dialyzer. In Step 31 the blood side 124 function is a forward rinse and in Step 35 it is a reverse rinse. Thus, in either case, there is rinse water in the arterial and venus blood side tubes 24 and 26 respectively. In order to begin the analysis, the valves are placed in their normal condition on both the blood and dialysate sides. On the blood side 124, this would require closing either the valve $V_2$ in the case of a hollow fiber dialyzer or opening the valve $V_7$ and closing the valves $V_8$ and $V_{10}$ in the case of a parallel plate or coil dialyzer. In this condition, there is effluent remaining in the arterial blood side drain line 146. As has been described, the blood analysis is performed by the blood analyzer 152. A metered amount of the chemical reagent 188 is infused into the plastic insert 186 and reacts with the effluent. The chemical reagent 188 is preferably a hemoglobin reagent. Such blood test compositions are disclosed in U.S. Pat. Nos. 3,012,976 and 3,092,463 which are herein incorporated by reference. After metering in the chemical reagent 188, the system delays ten seconds. The differential amplifier 206 then compares the voltage outputs from the first and second photocells 202 and 204. The differential amplifier 206 is adjusted to produce an output signal on line 207 if the content of blood components in the effluent is greater than about 2-4 milligram of hemoglobin per 1-200 milligrams of effluent. During this first blood level analysis, the "first blood level analysis" light 86 is lit. If the dialyzer passes this blood level test, the system cycles forward to Step 48, which is the first step in the pressure leak test, which will hereinafter be described. If the dialyzer does not pass the first blood level analysis, the process is incremented one step to Step 37, which is an air purge as will more specifically now be described.

Steps 37 and 38 represent a two step sub-sequence in which first the dialysate side 122 and then the blood side 124 are submitted to an air purge. The function of the corresponding dialyzer side in each step is open to drain. Thus, in step 37, the blood side 124 is squeezed from the pressure of the dialysate side 122 air purge, thereby expelling and dislodging blood components. In Step 38, the dialysate side 124 is squeezed while the blood side 122 undergoes an air purge.

Step 37 requires thirty seconds to complete. The valve $V_6$ is closed thereby closing the arterial dialysate side drain line 126. The valve $V_9$ is closed thereby closing the venus side drain line 138. The valve $V_{12}$ is opened thereby opening arterial dialysate side pressure line 138. Activation of the pressure pump $P_{14}$ produces a flow of air through the dialysate side 122, thus producing the air purge.

Step 38 requires thirty seconds to complete. The air pressure pump $P_{14}$ remains on. The valve $V_7$ is closed thereby closing the arterial blood side drain line 146. The valve $V_8$ is closed thereby closing the venus blood side drain line 166. Opening of the valve $V_{11}$ and the activation of air pressure pump $P_{14}$ produces a flow of air through the blood side 124 and the described air purge. While Steps 37 and Step 38 are in progress, the "purge" light 88 is lit.

Step 39 begins the first detergent cycle and requires three minutes to complete. The blood side 124 control sequence opens the valve $V_3$ and turns the peroxide pump $P_{13}$ on. The opening of the valve $V_3$ opens the blood side detergent line 162 so that peroxide can flow into the blood side 124 from pump $P_{13}$ and the reservoir 170. The valve $V_8$ remains closed from Step 38, and thus the blood side 24 of the dialyzer 18 will be filled with peroxide. The dialysate side 122 control sequence places all valves in a normal condition, so that the dialysate side 122 is open to drain.

The next step, Step 40, requires four minutes to complete. There are no changes in the blood dialysate side control sequence. The blood side control sequence closes the valve $V_3$ and turns the pressure pump $P_{13}$ off. This produces a delay function, with the blood side 124 remaining filled with peroxide for the four minute step.

Step 41 requires three minutes to complete. The blood side control sequence opens the valve $V_2$ and turns the R.O. water pump $P_{17}$ on. This produces a forward rinse in the blood side 124, thereby flushing the peroxide and blood components out and into the drain line. The dialysate side 122 control sequence places all valves in a normal condition, producing an open drain condition on the dialysate side 122. While Steps 39, 40 and 41 are in progress, "detergent cycle 1" light 90 is lit.

Steps 42 and 43 each require thirty seconds to complete and represent a two step air purge sub-sequence identical to the sub-sequence of Steps 37 and 38. While Steps 42 and 43 are in progress, "air purge" light 92 is lit.

Step 44 requires two minutes to complete and begins the second detergent cycle. The blood side control sequence opens the valve $V_2$ and closes the valve $V_8$. The valve $V_7$ is opened. The sodium hypochlorite pump $P_{16}$ is turned on. The opening of the valve $V_2$ opens the blood side 124 to the hypochlorite line 161, and the closing of the valve $V_8$ closes the venus blood side drain line 166, thereby allowing the blood side 124 to fill. Turning the sodium hypochlorite pump $P_{16}$ on fills the blood side 124 of the dialyzer with sodium hypochlorite obtained from the sodium hypochlorite reservoir 176. The dialysate side 122 control sequence places all valves in their normal position, producing an open drain condition on the dialysate dise 122.

Step 45 requires two minutes to complete. The valve $V_2$ is closed and the pump $P_{16}$ is turned off for the blood side control sequence. This produces a static condition in which the blood side 124 is filled with the sodium hypochlorite for a period of two minutes. There is no change on the dialysate side 122 of the dialyzer and the condition is, therefore, open to drain.

Step 46 requires two minutes to complete. The blood side control sequence opens the valve $V_2$ and turns the R.O. water pump $P_{17}$ on. This produces a forward rinse on the dialysate side 122, thereby flushing out the sodium hypochlorite and blood components. The dialysate side 122 valves remain in their normal position and the dialysate side is thereby open to drain. While Steps 44, 45 and 46 are in progress, the "detergent cycle 2" light 94 is lit.

Steps 47 and 48 represent another air purge sub-sequence identical to the sub-sequence comprising Steps 37 and 38. While steps 47 and 48 are in progress, "air purge" light 96 is lit.

Step 49 begins the pressure leak test and requires 30 seconds to complete. The blood side control sequence closes the valves $V_7$ and $V_8$ and opens the valve $V_{11}$. In addition the air pressure pump $P_{14}$ is turned on. The valve $V_7$ closes the arterial blood side drain line 146 and the valve $V_8$ closes the venus blood side drain line 166. The opening of the valve $V_{11}$ and the activation of the air pressure pump $P_{14}$ thereby serves to pressurize the blood side 124. The valves on the dialysate side 122 are in their normal condition, and the dialysate side is, therefore, open to drain.

Step 50 requires 30 seconds to complete and comprises the performance of a pressure leak test by means of a pressure sensor 158. The blood side control sequence closes the valve $V_{11}$ and turns the pump $P_{14}$ off. A preferred pressure sensor which is commercially available is Bell & Howell Model 4-424-000-1.

The pressure sensor 158 measures the pressure drop from the blood side 124 over a ten second period. If the pressure drop is no more than ten millimeters of mercury over the ten second period, the dialyzer passes the pressure leak test and the next step in the process is then sequenced. If the pressure drop is more than ten millimeters of mercury over the ten second period, the dialyzer fails the test and the further cleaning sequence is inhibited. This criterian of ten millimeters of mercury over a ten second period was chosen since it represents a generally recognized criteria for all dialyzers. While Steps 49 and 50 are in progress, "pressure leak test" light 98 is lit. If the dialyzer fails the pressure leak test, the "pressure leak test failure" light 100 is lit.

Step 51 requires four minutes to complete. The blood side control sequence closes the valve $V_7$ and opens the valves $V_8$ and $V_{10}$. The R.O. water pump $P_{17}$ is turned on. Closing the valve $V_7$ closes the arterial blood side drain line 146, while opening the valve $V_8$ opens the venus blood side drain line 166. The opening of the valve $V_{10}$ and the turning on of the R.O. water pump thereby produces a reverse rinse through the blood side 124. The dialysate side 122 control sequence opens the valve $V_1$ and maintains the pump $P_{17}$ on. This produces a forward rinse on the dialysate side 122.

Step 52 requires three minutes to complete. The blood side control sequence opens the valve $V_{12}$ and maintains the R.O. water pump $P_{17}$ on. This produces a forward rinse through the blood side 124. The valves in the dialysate side 122 are in their normal position, producing an open drain condition on the dialysate side 122. While Steps 51 and 52 are in progress, "rinse" cycle light 102 is lit.

Step 53 represents the second blood level analysis and is the same as Step 36. Unlike Step 36, however, if the dialyzer 18 fails this blood level analysis, the dialyzer 18 is rejected, and all further cleaning sequencing is inhibited. While Step 53 is in progress, the "second blood level analysis failure" light 106 is lit.

The next step in the process, Step 54, is the ultrafiltration test. This test actually comprises a sub-sequence of three steps, i.e., Steps 54a-c. The test indicates the hydraulic resistance of the membrane 123 of the dialyzer to flow. The measurement may also be made in terms of the capacity of the membrane 123 to transmit fluids. Step 54a requires 30 seconds to complete. The blood side control sequence opens the valve $V_2$, closes the valve $V_7$ and turns the RO water pump $P_{17}$ on, which allows the blood side 124 to fill with RO water. The dialysate side control sequence is to place the valves in their normal position, therefore, functioning to open the dialysate side to drain. Step 54b requires 30 seconds to complete. The blood side control sequence is to open the valve $V_{11}$ and turn the pressure pump $P_{14}$ on. This sequence applies an air pressure of 10 pounds per square inch to the blood side 124. The dialysate side control sequence and functions are the same as is Step 54a. Step 54c requires 20 seconds to complete. The blood side control sequence is to close the valve $V_{11}$ and to turn the pressure pump $P_{14}$ off. After a three minute wait, the pressure sensor 158 measures the ultrafiltration rate. The dialysate side control sequences and function remains the same as in the previous steps. If the pressure measurement is not less than 250 mm of mercury, nor more than 350 mm of mercury, the dialyzer passes the ultrafiltration test. If the pressure is more than 350 mm of mercury, this indicates that the membrane 123 is clogged with blood components or other matter, and is therefore not acceptable. Conversely, if the pressure is less than 250 mm of mercury, this indicates an abnormality in the membrane 123, such as, a tear. If the dialyzer fails this test, the dialyzer is rejected. While the ultrafiltration rate test is in progress, the "ultrafiltration rate test" light 108 is lit. A failure of the dialyzer is shown by the lighting of the "ultrafiltration rate test failure" light 110. The ultrafiltration rate analyzer is the pressure sensor 158 which was used in the pressure leak test described above. The preferred analyzer is the commercially available Bell & Howell model 4-424-000-1.

The dialysate side 122 control sequence places the valves in their normal position and, therefore, the dialysate side 122 is open to drain during the ultrafiltration rate test.

The ultrafiltration rate test is the last of the three basic tests which are performed during the cleaning process to determine whether the dialyzer 18 will be able to be reused. The three basic tests are the blood pressure test, the pressure leakage test and the ultrafiltration rate test. Each indicates the reusability of the dialyzer being cleaned, and has a predetermined criterian which must be met in order for the dialyzer to pass. If the dialyzer 18 fails any one of the three tests, the dialyzer 18 is rejected and the cleaning sequence is terminated. The dialyzer status is displayed by the dialyzer status lights 72 and 74. Thus, if the dialyzer is acceptable, the dialyzer status light 72 is lit, whereas, if the dialyzer is rejected, the dialyzer reject light 74 is lit.

These tests represent an important feature of the invention, since they provide a check on the cleaning process during its progress. An early recognition of an unacceptable dialyzer 18 provides time and cost savings to the process, as well as insuring that any dialyzer 18 which is to be used meets all of the specified criteria.

Steps 55 and 56 represent another air purge subsequence identical to the sub-sequence comprising Steps 37 and 38. While Steps 55 and 56 are in progress, "air purge" light 112 is lit.

The next step in the process is the disinfectant cycle, which begins with Step 57. In Step 57, the blood side 124 control sequence opens the valve $V_4$, opens the valve $V_7$ closes valve $V_8$ and turns the formalin pump $P_{15}$ on. The closing of the valve $V_8$, closes the venus blood side drain line 166. The opening of the valve $V_4$ opens the venus formalin line 164. When the formalin pump $P_{15}$ is actuated, formalin is pumped into the blood side 124. As earlier discussed, formalin is only one of several possible disinfectants. Any suitable sterilizing medium is within the scope of this invention. While the blood side is being filled with formalin, the valves of the dialysate side are in a normal position, and the dialysate side is thereby open to drain.

In Step 58, the valve $V_4$ is closed, so that the blood side 124 is then in a static condition filled with formalin. The dialysate side 122 control sequence opens the valve $V_5$, opens the valve $V_6$, closes $V_9$ and maintains the pump $P_{15}$ on. The opening of the valve $V_5$ opens the venus dialysate side formalin line 134, while the closing of the valve $V_9$ closes the venus dialysate side drain line 138. When the pump $P_{15}$ is actuated, formalin is pumped into the dialysate side 122 in a dialysate fill function.

In Step 59, no change occurs on the blood side 124 so that the blood side 124 remains filled with formalin. The valve $V_5$ is closed and the pump $P_{15}$ turned off and, therefore, the dialysate side 122 is also in a static condition filled with formalin. The dialyzer can be maintained in this sterilized condition for as long as necessary. While Steps 57, 58, and 59 are in progress, "disinfectant cycle" light 114 is lit.

Upon completion of the disinfectant cycle, the cleaning process is complete, which is shown by lighting of the "cleaning complete" light 115. The dialyzer 18 is then manually disconnected. The operator then has a choice with respect to resequencing the machine to prepare for cleaning the next dialyzer. First, he may manually actuate the station preparation switch 40 which sets the station at Step 3 to begin the station preparation cleaning sequence. However, if the station has recently been disinfected from the disinfect cycle used to complete the cleaning of the previous dialyzer, the operator may press reset switch 118 which resets the sequence to Step 13. This begins the identification phase and in effect bypasses the station preparation cycle.

The next step is to manually clean the dialyzer 18 externally with disinfectant, and to then manually bag and seal the dialyzer before storage. This step is important for preventing or reducing the possibility for cross contamination or the growth of virus such as hepatitis.

The last step in the process is to actuate the secured station switch 120, which produces the machine operations of disinfecting the control and hydraulic circuits and to secure the station.

Having described the cleaning process and the mechanical hardware, the electronics utilized to control this process will be described with reference to FIG. 3. A standard electronic memory, shown generally as 208, consists of an address portion 210 and a data portion 212. The address portion 210 provides a numerical series corresponding in order to the step sequences of the process. Each address is used to access a corresponding data word which provides the information necessary to perform a particular process step. More than one word may be required for some steps, as where there is a measurement to be taken.

An address register 214 is used to access the address portion 210 of the memory bank 208. This will, in turn, access the particular data word which corresponds to that step. Thus, for example, when a particular number is placed in the register 214, information from the data portion 212 of the memory bank 208, corresponding to an address 210 identical to the particular number, is transmitted to a data register 216.

The data word provided at the data register 216 by the memory 208 is divided into several bit positions. In the implementation shown, these bit positions are hard wired to various control elements, registers, etc., as described below. Thus, a zero or one data bit, placed in a particular bit location of the register 216, at a particular cleaning step, by the memory 208, will activate or deactivate a particular control element, as described below.

As shown in the Figure, the first portion of the word consists of multiple bits which control the panel light system relating to the sequence of cleaning steps, phases 1 and 2, beginning with the prerinse step to notify the operator of the progress of the cleaning cycles. These lights are found in the Sections 75 and 77 on panel 36 as described earlier. As an example, the first bit 218 controls a single one of the panel lights. Thus, the "prerinse" light 80 is lit if the bit 218 is one, but is not lit if the bit 218 is zero. Each of the panel lights of cleaning phases 1 and 2, would have a corresponding data bit in the first portion of the data word. All of these bits are not shown, to simplify the drawing. Thus, for the various cleaning steps, particular lights on the control panel 36 should be illuminated. Each data field 212 in the memory 208 will include a control bit for each panel light, so that, when the data field is transferred to the register 216, the proper lights will be activated.

The second portion of the data word relates to information for the valves, pumps and data reader. For example, a one data bit placed at location 219 when the data word is transferred from the memory 208, would produce a signal to a valve driver 221 which, in turn, would open or close a particular valve 223. The same principal is true with respect to the pumps, in which a one in a selected bit location activates a selected pump, while a zero produces a signal to a pump driver which turns the pump off. Finally, in this same data group, a one data bit in an additional predetermined location within the data word is used for actuating a data reader 240 which will then receive photo-optical input 239 which is used to read the dialyzer type and patient number, as described earlier. As shown with the lights, all of the control bits are not shown.

A third portion of the data word provides the time required to perform each particular step, written in binary code. At the beginning of each step, this time code is loaded into the counter 225. The counter is continually supplied with pulses from a clock 227, and counts down from the loaded time value at a rate determined by the frequency of the clock 227. When the count is exhausted, the down counter produces a signal on line 229 indicating that the loaded time value has expired.

The next portion of the data word is a group of decision bits, the first bit 222 of which is used to activate the blood level analysis test described above. A one data bit at location 222 indicates that no blood level analysis is to be performed, at a particular process step. This one bit provides an input through an AND gate 224 to and AND gate 220. Thus, when the binary decision bit 222 is a one, the AND gate 220 will permit an output signal on line 229, indicating that the count is exhausted from the down counter 225, to increment the address register 214, thereby allowing the process to continue to the next step in the cleaning sequence.

Referring again to the decision bit 222, if the binary information is a zero at a particular process step, this means that a decision must be made. The binary zero at the bit 222 is inverted at an inverter 230, and transmitted to enable an output signal from a blood analysis address register 232. The blood level analysis register 232 contains an address C and an address D.

The address C is the address for step 48, and is enabled by a low signal from the differential amplifier 206. Thus, if the blood level analysis test, described previously, indicates a satisfactory blood level, the address C will be loaded into the address register 214, containing the cleaning process at step 48. However, if the blood level is determined to be high from the blood level analysis, address D provides the address for step 37, which will be loaded into the address register 214. Thus, if the dialyzer fails to pass the first blood level analysis test, the cleaning process will proceed at step 37. This system therefore, allows the selection of cleaning step sequences depending upon the pass or failure of the first blood level analysis test. In short, if the dialyzer fails the test, it undergoes additional step Nos. 37 through 47, whereas, if the dialyzer passes the test, the cleaning procedure jumps to step 48.

A similar decision bit 233 is used to control the second blood level test at step 53. Thus, a binary zero at the bit 233 during a particular cleaning step is inverted at an inverter 239, and used to select addresses E or F for loading into the register 214, to provide continued cleaning if the dialyzer passes the test, or a stop in the cleaning process if it fails. This stop command will be described below. Likewise, the pressure level test will enable one of registers G or H, when the decision bit 235 is loaded with a zero and inverted at an inverter 241 for particular process step, to continue the cleaning process at step 51, or to stop the cleaning process, respectively. Finally, the ultrafiltration rate test will enable one of the registers I or J, when the decision bit 237 is loaded with a zero, and inverted at an inverter 243, to continue the process at step 54 or stop the cleaning process, respectively.

The next decision bit 234 requires a determination of the particular dialyzer type which is sensed by the data reader. If the decision bit 234 contains a zero code, a signal will be produced which is inverted at an inverter 236, which enables the dialyzer type address register 238. Dialyzer type address register 238 contains an address A and an address B portion. The particular dialyzer type, as was discussed before, is determined by the data reader 240. Upon identifying the dialyzer type, the data reader inputs a signal to a dialyzer type register 242, enabling either the A or B address. The dialyzer type is coded either as a zero, which refers to a hollow fiber dialyzer or a one, which is identified as a parallel plate or coil type dialyzer. The information bit with respect to the hollow fiber type dialyzer is shown as 244 and the bit with respect to the parallel plate or coil dialyzer is shown as 246. Data bit 244, if a one, will produce an enable signal to the address A portion of the dialyzer type address register 238. Similarly, if the dialyzer type is a parallel plate or coil type dialyzer, a signal will be produced from data bit 246 to enable the address B portion of the dialyzer type address register 238. The address A provides the address for step 26, whereas, the address B provides the address for step 32. In summary, if decision bit 234 is zero, it will produce a signal which is transferred to enable the dialyzer type address register 238. Then, depending upon the dialyzer type which is sensed by the data reader, the address register 241 will be loaded with either step 26 address, corresponding to a cleaning process for a hollow fiber type dialyzer, or step 32, corresponding to a cleaning process for a parallel plate or coil dialyzer.

It should be noted that using the process described above, decision bit 222 will be a zero only at the location in the memory 208 which stores the data for process step 36, bit 233 only at step 53, bit 234 only at step 25, bit 235 only at step 50, and bit 237 only at step 54.

As discussed above, in order to begin the cleaning sequence, the operator pushes the power on switch 38. At the end of the cleaning sequence, the operation may actuate the station preparation switch 40, which produces a signal that enables a third step address register 256 which, in turn, loads the address register 214 with the address of the third step of the process, i.e., the beginning of the station preparation cycle. However, if the machine is already in a sterilized condition due to a recently completed disinfectant cycle sequence during the cleaning of a previous dialyzer, the operation may press the reset switch 118. The switch 118 produces a signal that enables an address 254 which provides the address for step 13. The address 254 will thereby load the address register 214 with the address of the thirteenth step of the process. This bypasses the station preparation cycle and returns the station to the beginning of the identification phase discussed earlier.

Three data bits 272, 274 and 276, are utilized to illuminate lights 48, 50 and 52, respectively, on the front panel 36. When one of these bits is loaded with a one from a data word from the memory 208, a signal will be inputed to the AND gate 224 to allow incrementing the sequence. When one of the bits 272, 274, and 276 is loaded with a zero, the zero is inverted at three inverters 288, 290 and 292, respectively and a specific light on the panel 36 will be lit. In addition, each of these bits is connected as one input of an AND gate 278, 280 and 282, respectively. The other input of these AND gates is connected to the dialyzer type register 242, a patient number register 284, and a station number register 286, to enable the gates 278, 280, 282, when the operator has input, respectively, the dialyzer type, patient number or station number. As an example, when the bit 272 is a zero, at a particular process step, the light 48 will illuminate, notifying the operator that the station number data should be input. The operator signal will then depress the particular station number switch which corresponds to its particular station. Pressing the switch 42 on the panel 36 enables a station number register 273 which is loaded with the preparation number and inputs it into the station number register 286. The station number 286 after receiving the station number identification will enable the station number display 44. The combination of the station number input at 286, and a zero bit at bit position 272, inverted at 288, will produce an output signal from an AND gate 278 to the increment line, incrementing the address register 214 to the next step in the cleaning sequence. Likewise, the inverters 290 and 292 invert a zero bit at positions 274 and 276 to illuminate the lights 50 and 52, and to enabel the AND gates 280 and 282 when a patient number or dialyzer type is present at registers 284 and 282, respectively. The output of the AND gates 218, 280 and 282 passes through an OR gate 203 which, in turn, leads to incrementing of the address register 214 when the proper data is input to the system. If the proper data is not inputed into the system at the proper step of the sequence, all further sequencing is thereby inhibited.

It will be noted that, in the cleaning sequence described above, bit positions 272, 274 and 276 of the register 216 will be loaded with a zero only at steps 13, 14 and 15 respectively.

The ability of the system to inhibit further sequencing will now be described.

A stop bit 260, when provided with a zero bit in a special command word from the memory 208, is utilized to inhibit further system sequencing. This step is used in the case of a failure of the dialyzer to meet specific cleaning tests, specifically, those tests which occur at steps 50, 53, and 54 that is, those tests which generate an address from address F, address H, or address J registers. Each of these address registers F, H and J, will provide the same address signal to the memory 208 to provide this special data word. The data word provides a normal position for all valves and pumps within the system, while the zero bit at location 260, through the AND gate 224, will inhibit the AND gate 220 and thus, inhibit further system sequencing. In addition, the zero bit at position 260 through the inverter 261, will energize the dialyzer reject status light 74 on the panel 36. As an additional indication of the source of dialyzer failure, when an output signal is provided by address F, H or J, a specific malfunction light 106, 100, or 110 respectively will be illuminated on the front panel 36.

A second step bit 262 is used to inhibit further sequencing if a malfunction occurs in the system during cycling. If stop bit 262 is zero, it disables the system, by inhibiting the AND gate 220. The address of the memory location, containing a zero bit in location 262 is provided by an address K register 264 which is connected by an OR gate 266 to the system malfunction sensors. When a malfunction occurs, this address is loaded into the address register 214, providing the stop command instruction to the data register, and a zero bit in the bit position 262. All other valves will be placed in their normal position. Each malfunction sensor is, in addition, connected to a specific light 54–70 on the panel 36 to warn the operator of the location of the malfunction.

The use of the patient number to indicate the number of times a dialyzer has been cleaned, as well as its use in preventing a rejected dialyzer from being reused, will now be described.

A dialyzer use register 302 stores, as separate data bytes, a list of patient numbers 304 correlated with a count designation 306. Initially, the count designations 306 will all contain a zero count. Whenever a patient number is entered at the data reader 240, this patient number is input to a search and access circuit 308, which cycles the data in the memory 302 until a matching patient number has been located. Thus, in effect, the patient number from the data input 240 is used to address the memory 302. Once addressed, the memory 302 supplies to a register 310 the use count, that is, the number of times the dialyzer has previously been cleaned. The register 310 is connected to an incrementer 312, which adds a count of 1 to the previous number of uses, and resupplies this new count to the data field 306 of the memory 302 in the same location where the count was initially accessed. Thus, the count for this specific patient will be incremented. The incrementer 312 is also connected to a printer 250, which supplies, with other printed output data, the total number of times that this patient's dialyzer has been cleaned at the end of the current cleaning cycle. It should be understood that, when new patients are entered into the system, new patient numbers are placed in the patient number field 304 of the memory 302, with a zero count.

The memory 302 has, as another important function, prohibiting use of a dialyzer which has previously been rejected during a cleaning cycle. The output of the inverter 261, described previously, is connected to a register 314 containing all zeros for the entire data field 304 and 306 of the memory 302. Since the memory 302 will be addressed at the beginning of the cleaning cycle to the particular patient whose dialyzer is being cleaned during the cleaning process, a failure signal from the inverter 261 will enable the zero register 314 to write zeros for the patient number and the number of uses, thus, in effect, erasing the patient number from the memory 302. At a later time, an operator, using a memory data reader 316 and an additional photo-optical input source 318, can search the memory 302 to determine whether the patient number on a specific dialyzer exists in the memory 302. If the patient number exists in the patient number field 304 of the memory 302, an output signal will be provided on line 320, illuminating a light on the front panel 36 notifying the operator that the dialyzer is satisfactory for additional use. If, on the other hand, the patient number has been removed from the memory 320 by writing zeros from the register 134, a signal will appear on line 322, illuminating a light on the panel 36, notifying the operator that the dialyzer should be discarded and not used.

Data bit 248 contains the data information necessary to enable the printer 250. A one bit produces a signal enabling the printer 250 to print out the particular information sought to be recorded, for example, the day, data and time of the cleaning operation which is generated by a day, data and timeclock 252. In addition, the dialyzer type sensed by the data reader 240 and inputed to the dialyzer type register 252, the patient number also sensed by the data reader and inputed to the patient number register 284, and the station number, which is punched in by the operator using switch 42 and inputed to station number register 286, are all printed out when printer 250 is enabled.

TABLE 1

| STEP. NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| 3 | 17 sec. | $V_2$ open<br>$P_{17}$ on | Forward rinse | $V_1$ open<br>$P_{17}$ on | Forward rinse |
| 4 | 34 sec. | $V_7$ closed<br>$V_8$ open<br>$V_{11}$ open<br>$P_{14}$ on | Air purge | $V_1$ open<br>$P_{17}$ on | Forward rinse |
| 5 | 34 sec. | $V_7$ closed<br>$V_8$ open<br>$V_{11}$ closed<br>$V_{10}$ open<br>$P_{17}$ on | Reverse rinse | $V_1$ open<br>$P_{17}$ on | Forward rinse |
| 6 | 34 sec. | $V_2$ open<br>$P_{17}$ on | Forward rinse | $V_1$ open<br>$P_{17}$ on | Forward rinse |
| 7 | 34 sec. | $V_7$ closed<br>$V_8$ open<br>$V_{11}$ open<br>$P_{14}$ on | Air purge | $V_1$ open<br>$P_{17}$ on | Forward rinse |
| 8 | 34 sec. | $V_7$ closed<br>$V_8$ open<br>$V_{11}$ closed<br>$V_{10}$ open<br>$P_{17}$ on | Reverse rinse | $V_1$ open<br>$P_{17}$ on | Forward rinse |
| 9 | 34 sec. | $V_2$ open<br>$P_{17}$ on | Forward rinse | $V_1$ open<br>$P_{17}$ on | Forward rinse |
| 10 | 34 sec. | $V_7$ closed<br>$V_8$ Open<br>$V_{11}$ Open<br>$P_{14}$ On | Air purge | $V_1$ Open<br>$P_{17}$ On | Forward rinse |
| 11 | 34 sec. | $V_7$ Closed<br>$V_8$ Open<br>$V_{11}$ Closed<br>$V_{10}$ Open<br>$P_{17}$ On | Reverse rinse | $V_1$ Open<br>$P_{17}$ On | Forward rinse |

TABLE 2

| STEP. NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| 17 | 17 sec. | $V_2$ open<br>$P_{17}$ on | Forward rinse | $V_1$ open<br>$P_{17}$ on | Forward rinse |
| 18 | 34 sec. | $V_7$ closed<br>$V_8$ open<br>$V_{11}$ open<br>$P_{14}$ on | Air purge | $V_1$ open<br>$P_{17}$ on | Forward rinse |
| 19 | 34 sec. | $V_7$ closed<br>$V_8$ open<br>$V_{11}$ closed<br>$V_{10}$ open<br>$P_{17}$ on | Reverse rinse | $V_1$ open<br>$P_{17}$ on | Forward rinse |

TABLE 2-continued

| STEP. NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| 20 | 34 sec. | $V_2$ open<br>$P_{17}$ on | Forward rinse | $V_1$ open<br>$P_{17}$ on | Forward rinse |
| 21 | 34 sec. | $V_7$ closed<br>$V_8$ open<br>$V_{11}$ open<br>$P_{14}$ on | Air purge | $V_1$ open<br>$P_{17}$ on | Forward rinse |
| 22 | 34 sec. | $V_7$ closed<br>$V_8$ open<br>$V_{11}$ closed<br>$V_{10}$ open<br>$P_{17}$ on | Reverse rinse | $V_1$ open<br>$P_{17}$ on | Forward rinse |
| 23 | 34 sec. | $V_2$ open<br>$P_{17}$ on | Forward rinse | $V_1$ open<br>$P_{17}$ on | Forward rinse |
| 24 | 34 sec. | $V_7$ Closed<br>$V_8$ Open<br>$V_{11}$ Open<br>$P_{14}$ On | Air purge | $V_1$ Open<br>$P_{17}$ On | Forward rinse |
| 25 | 34 sec. | $V_7$ Closed<br>$V_8$ Open<br>$V_{11}$ Closed<br>$V_{10}$ Open<br>$P_{17}$ On | Reverse rinse | $V_1$ Open<br>$P_{17}$ On | Forward rinse |

TABLE 3

| STEP NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| 26 | 4 Min. | $V_8$ Open | "Squeezing" of blood side reverse ultra-filtration | $V_1$ Open<br>$V_6$ Closed<br>$P_{17}$ On | Forward rinse |
| 27 | 2 Min. | $V_7$ Closed<br>$V_8$ Open<br>$V_{10}$ Open<br>$P_{17}$ On | Reverse rinse | $V_9$ Open | Drain open |
| 28 | 2 Min. | $V_2$ Open<br>$P_{17}$ On | Forward rinse | $V_9$ Open | Drain open |
| 29 | 4 Min. | $V_8$ Open | "Squeezing" of blood side-reverse ultra-filtration | $V_1$ Open<br>$V_6$ Close<br>$P_{17}$ On | Forward rinse |
| 30 | 2 Min. | $V_7$ Closed<br>$V_8$ Open<br>$V_{10}$ Open<br>$P_{17}$ On | Reverse rinse | $V_9$ Open | Drain open |
| 31 | 2 Min. | $V_2$ Open<br>$P_{17}$ On | Forward rinse | $V_9$ Open | Forward rinse |

TABLE 4

| 32 | 4 Min. | $V_2$ Open<br>$P_{17}$ On | Forward rinse | $V_9$ Open | Drain open |
| 33 | 4 Min. | $V_7$ Closed<br>$V_8$ Open<br>$V_{10}$ Open<br>$P_{17}$ On | Reverse rinse | $V_9$ Open | Drain open |
| 34 | 4 Min. | $V_2$ Open<br>$P_{17}$ On | Forward rinse | $V_9$ Open | Drain open |
| 35 | 4 Min. | $V_7$ Closed<br>$V_8$ Open<br>$V_{10}$ Open<br>$P_{17}$ On | Reverse rinse | $V_9$ Open | Drain open |

TABLE 5

| STEP NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| 36 | 1 Min. | Valves in normal position | Blood test of effluent | Valves in normal position | Open to drain |
| 37 | 30 sec. | Valves in normal position | Open to drain | $V_6$ Closed<br>$V_9$ Open<br>$V_{12}$ Open<br>$P_{14}$ On | Air Purge |
| 38 | 30 sec. | $V_7$ Closed<br>$V_8$ Open<br>$V_{11}$ Open<br>$P_{14}$ On | Air purge | Valves in normal condition | Open to drain |
| 39 | 3 Min. | $V_3$ Open | Peroxide | Valves in | Open to drain |

TABLE 5-continued

| STEP NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| | | $V_7$ Open<br>$V_8$ Closed<br>$P_{13}$ On | fill | normal condition | |
| 40 | 4 Min. | $V_3$ Closed<br>$P_{13}$ Off | Peroxide wait | No change | Open to drain |
| 41 | 3 Min. | $V_2$ Open<br>$P_{17}$ On | Peroxide flush forward rinse | Valves in normal condition | Open to drain |
| 42 | 30 sec. | Valves in normal position | Open to drain | $V_6$ Closed<br>$V_9$ Open<br>$V_{12}$ Open<br>$P_{14}$ On | Air purge |
| 43 | 30 sec. | $V_7$ Closed<br>$V_8$ Open<br>$V_{11}$ Open<br>$P_{14}$ on | Air purge | Valves in normal condition | Open to drain |
| 44 | 2 Min. | $V_2$ Open<br>$V_7$ Open<br>$V_8$ Closed<br>$P_{16}$ On | Sodium hypochlorite fill | Valves in normal condition | Open to drain |
| 45 | 2 Min. | $V_2$ Closed<br>$P_{16}$ Off | Sodium hypochlorite wait | No change | Open to drain |
| 46 | 2 Min. | $V_2$ Open<br>$P_{17}$ On | Sodium hypochlorite flush | Valves in normal position | Open to drain |
| 47 | 30 sec. | Valves in normal position | Open to Drain | $V_6$ Closed<br>$V_9$ Open<br>$V_{12}$ Open<br>$P_{14}$ On | Air Purge |
| 48 | 30 sec. | $V_7$ Closed<br>$V_8$ Open<br>$V_{11}$ Open<br>$P_{14}$ On | Air Purge | Valves in normal condition | Open to drain |
| 49 | 30 sec. | $V_7$ Closed<br>$V_8$ Closed<br>$V_{11}$ Open<br>$P_{14}$ On | Blood side pressurized | Valves in normal position | Open to drain |
| 50 | 30 sec. | Perform pressure leak test<br>$V_{11}$ Closed<br>$P_{14}$ Off | Measure pressure drop over 10 seconds | Valves in normal position | Open to drain |
| 51 | 4 Min. | $V_7$ Closed<br>$V_8$ Open<br>$V_{10}$ Open<br>$P_{17}$ On | Reverse rinse | $V_1$ Open<br>$P_{17}$ On | Forward rinse |
| 52 | 3 Min. | $V_2$ Open<br>$P_{17}$ On | Forward rinse | Valve in normal position | Open to drain |
| 53 | 1 Min. | Valves in noraml position | Blood test of effluent | Valve in normal position | Open to drain |
| 54a | 30 Sec. | $V_2$ Open<br>$V_7$ Closed<br>$P_{17}$ On | Fill with R/O water | Valves in normal position | Open to drain |
| 54b | 30 Sec. | $V_{11}$ Open<br>$P_{14}$ On | Apply 10 psi | Valves in normal position | Open to drain |
| 54c | 20 Sec. | $V_{11}$ Closed<br>$P_{14}$ Off | Measure ultrafiltration rate after 3 minute wait | Valves in noraml position | Open to drain |
| 55 | 30 Sec. | Valves in normal position | Open to drain | $V_6$ Closed<br>$V_9$ Open<br>$V_{12}$ Open<br>$P_{14}$ On | Air purge |
| 56 | 30 Sec. | $V_7$ Closed<br>$V_8$ Open<br>$V_{11}$ Open<br>$P_{14}$ On | Air purge | Valves in normal condition | Open to drain |
| 57 | | $V_4$ Open<br>$V_7$ Open<br>$V_8$ Closed<br>$P_{15}$ On | Fill with formalin | Valves in normal position | |
| 58 | | $V_4$ Closed | Filled with formalin | $V_5$ Open<br>$V_6$ Open<br>$V_9$ Closed<br>$P_{15}$ On | Fill with formalin |

TABLE 5-continued

| STEP NO. | TIME | BLOOD SIDE CONTROL SEQ. | BLOOD SIDE FUNCTION | DIALYSATE SIDE CONTROL SEQ. | DIALYSATE SIDE FUNCTION |
|---|---|---|---|---|---|
| 59 | | No change | Filled with formalin | $V_5$ Closed $P_{15}$ Off | Filled with formalin |

We claim:

1. A system for cleaning a dialyzer having a blood side and a dialysate side separated by a membrane comprising:
   means for storing a first predetermined sequence of cleaning procedures, said first storing means providing first control signals;
   means for storing a second predetermined sequence of cleaning procedures, said second storing means providing second control signals;
   means for regulating the flow of a plurality of blood cleaning reagents through the dialysate and blood sides of the dialyzer;
   means responsive to said first control signals for automatically controlling said regulating means to provide said cleaning procedures in said first predetermined sequence;
   means for monitoring the condition of said dialyzer during said first predetermined sequence of cleaning procedures; and
   means responsive to said monitoring means for selectively controlling the sequencing of the cleaning procedures in said second predetermined sequence in response to the condition of said dialyzer to prohibit the use of defective dialyzers.

2. The system of claim 1 wherein said controlling means inhibits said second predetermined sequence of cleaning procedures.

3. The system of claim 1 wherein said controlling means alters the order of said second predetermined sequence of cleaning procedures.

4. The system of claim 1 wherein said controlling means selects specific steps from said second predetermined sequence of cleaning procedures to clean said dialyzer.

5. The system of claim 1 wherein said monitoring means measures indicia of useability of said dialyzer.

6. The system of claim 5 further comprising means for storing predetermined criteria which a dialyzer must meet in order to be useable.

7. The system of claim 6 wherein said controlling means inhibits said second predetermined sequence of cleaning procedures if said indicia of useability measured by said monitoring means do not meet said predetermined criteria.

8. The system of claim 1 wherein said monitoring means measures the level of blood components remaining in the blood side effluent of the dialyzer.

9. The system of claim 8 wherein said monitoring means measures the concentration of hemoglobin present in an effluent obtained from rinsing said blood side.

10. The system of claim 1 wherein said monitoring means measures pressure leakage from the blood side of said dialyzer.

11. The system of claim 1 wherein said monitoring means measures the pressure drop in a 10 second period from the blood side after said blood side has been pressurized.

12. The system of claim 1 wherein said monitoring means measures the ultra-filtration rate of a fluid through the membrane of the dialyzer over a period of time.

* * * * *